United States Patent
Vaquero Lopez et al.

(10) Patent No.: US 8,246,531 B2
(45) Date of Patent: Aug. 21, 2012

(54) INCUBATOR FOR NON-IONISING RADIATION IMAGING

(75) Inventors: Juan Jose Vaquero Lopez, Madrid (ES);
Manuel Desco Menendez, Madrid (ES);
Manuel Sanchez Luna, Madrid (ES)

(73) Assignee: Fundacion Para la Investigacion Biomedica del Hospital Gregorio Maranon, Madrid (ES)

( * ) Notice: Subject to any disclaimer, the term of this patent is extended or adjusted under 35 U.S.C. 154(b) by 64 days.

(21) Appl. No.: 12/735,096

(22) PCT Filed: Dec. 19, 2007

(86) PCT No.: PCT/ES2007/070214
§ 371 (c)(1),
(2), (4) Date: Dec. 9, 2010

(87) PCT Pub. No.: WO2009/077626
PCT Pub. Date: Jun. 25, 2009

(65) Prior Publication Data
US 2011/0125010 A1    May 26, 2011

(51) Int. Cl.
*A61G 11/00* (2006.01)
(52) U.S. Cl. ............... 600/22; 600/430; 600/473
(58) Field of Classification Search ............ 600/21, 600/22, 300, 407–431, 437–466, 473–480
See application file for complete search history.

(56) References Cited

U.S. PATENT DOCUMENTS

| | | | | |
|---|---|---|---|---|
| 3,858,570 A * | 1/1975 | Beld et al. | | 600/22 |
| 4,492,279 A * | 1/1985 | Speckhart | | 177/45 |
| 4,617,912 A * | 10/1986 | Beer et al. | | 600/22 |
| 5,149,030 A * | 9/1992 | Cockrill | | 248/129 |
| 5,387,177 A * | 2/1995 | Dunn | | 600/22 |
| 5,446,934 A * | 9/1995 | Frazier | | 5/655 |
| 5,616,115 A * | 4/1997 | Gloyd et al. | | 600/22 |
| 5,730,355 A * | 3/1998 | Lessard et al. | | 237/3 |
| 5,800,335 A * | 9/1998 | Koch et al. | | 600/22 |
| 5,935,055 A * | 8/1999 | Koch et al. | | 600/22 |
| 6,168,563 B1 * | 1/2001 | Brown | | 600/301 |
| 6,409,654 B1 * | 6/2002 | McClain | | 600/22 |
| 6,611,702 B2 * | 8/2003 | Rohling et al. | | 600/415 |
| 6,679,830 B2 * | 1/2004 | Kolarovic et al. | | 600/22 |
| 7,255,671 B2 * | 8/2007 | Boone et al. | | 600/22 |
| 7,278,962 B2 * | 10/2007 | Lonneker-Lammers | | 600/22 |
| 7,364,539 B2 * | 4/2008 | Mackin et al. | | 600/22 |
| 7,599,728 B2 * | 10/2009 | Feenan | | 600/411 |
| 7,691,048 B2 * | 4/2010 | Mahony et al. | | 600/22 |
| 7,966,678 B2 * | 6/2011 | Ten Eyck et al. | | 5/603 |
| 8,142,375 B2 * | 3/2012 | Gaspard | | 601/84 |
| 8,147,396 B2 * | 4/2012 | Srinivasan | | 600/22 |
| 2002/0082468 A1 * | 6/2002 | Goldberg et al. | | 600/22 |
| 2002/0173717 A1 * | 11/2002 | Rohling et al. | | 600/415 |
| 2003/0153805 A1 * | 8/2003 | Gryn et al. | | 600/22 |
| 2004/0106844 A1 * | 6/2004 | Lonneker-Lammers | | 600/22 |
| 2005/0113668 A1 * | 5/2005 | Srinivasan | | 600/411 |

* cited by examiner

*Primary Examiner* — Sanjay Cattungal
(74) *Attorney, Agent, or Firm* — Suzanne Kikel (57) ABSTRACT

An incubator for imaging with non-ionising radiation adapted for the care of newborn babies, which integrates a system projective or tomographic imaging system, or both simultaneously, which makes use of non-ionising radiation in the band of the electromagnetic spectrum included between ultraviolet light and far infrared, a system which can be used to view a subject (11) located in the incubator (19) such that this projective or tomographic image can be morphological or functional.

21 Claims, 7 Drawing Sheets

INCUBATOR FOR NON-IONISING RADIATION IMAGING

OBJECTIVE OF THE INVENTION

This invention refers, in general, to a life support system, to wit an incubator for intensive care for newborn babies, which includes a plane and a tomographic imaging system which makes use of non-ionising radiation.

STATE OF THE ART

The study of images of the lungs in newborn and prematurely-born babies is a very important indication using radiology, but it is not the only one. Extensive use is also made of this technique in the study of soft tissues for the diagnosis of congenital masses, in the study of bones when malformations or fractures are sought, to display the heart and the arrangement of blood vessels in the thorax, the distribution of abdominal gas, digestive tract and thoracic malformations, etc.

The individuals who have these pathologies are precisely those who run the greatest risk of developing complications due to the use of high doses of ionising radiation, such as X-rays for example, basically due to their immaturity, and this risk increases as the dose rises. The paradox is that the more immature the newborn baby, the higher the X-ray dose they usually receive.

The improvement in care during gestation, in the management of birth and of newborn premature babies means that these babies have survival rates which were unthinkable only 10 years ago. Survival rates for newborn babies with 25 weeks gestation now exceed 50% and reach 85% for those who are born at 29 weeks or more.

However, when a premature baby is born, if its immaturity is such that it has respiratory problems, radiology of their thorax is a common practice. The greater the degree of immaturity, the greater the respiratory problems and, therefore, the greater the need to use conventional portable radiology in intensive care units to view respiratory tracts and lungs.

In these cases it is necessary to aid newborn babies with systems which administer oxygen and increase the pressure in the lungs. This is normally achieved by means of different gas mixtures through small plastic cannulas in the nose or endotracheal tubes located in the lung. The diagnosis of the respiratory problem and the prevention of complications, the response to different treatments or the confirmation of the correct location of the tubes and catheters require conventional radiological studies which are carried out at the incubator. Even with awareness of the risk their use involves, there is currently no alternative to the use of conventional X-rays.

Therefore, the problem to be resolved is to avoid the use of X-rays in incubators as these make use of ionising electromagnetic radiation to pass through the human body and produce an image on a photographic plate or an electronic detector. The use of X-rays involves subjecting the individual under study, as well as the health care personnel who provide the service, to a dose of ionising radiation. This is why the requirement exists to have a suitable conditioned place for an apparatus to produce X-rays, which is sufficiently isolated by structures to prevent the dispersion of the X-rays outside of the area under study, such as lead-lined walls or screens. Obviously, the use of an incubator and the need to be close to the patient mean that these requirements are not met.

CHARACTERISATION OF THE INVENTION

This invention seeks to resolve or reduce one or more of the aforementioned disadvantages by means of an incubator as claimed in claim 1. Embodiments of the invention are established in the dependent claims.

One objective of the invention is to provide an incubator which incorporates an imaging system to display the position of different types of probes which are inserted into newborn babies, such as systems for assisted breathing, drainage of liquids or for feeding.

Another objective of the invention is to provide a means of covering these probes in order to increase the contrast between the biological tissue and the probes inserted into it.

A further objective of the invention is to provide the incubator with a device which enables a projective or tomographic, anatomical or functional, image to be made in any part of the body of a newborn baby.

Another objective of the invention is to permit the study of any desired subject who has respiratory problems, cardiac, digestive tract, bone, soft tissue or similar malformations.

A further objective still of the invention is to provide an imaging technique that, simply and safely, displays the lungs, heart structures, blood vessels, soft tissues, bones and the intraluminal gas in the digestive tract.

Another objective of the invention is to provide an incubator comprising a system for generating images based on low energy photons such as light, which consequently has no harmful effects on the biological tissue which is considered a turbid medium for this purpose.

A further objective of the invention is to use the system for generating images repeatedly without moving the subject under study in the incubator itself.

Still another objective of the invention is to provide the imaging system with a synchronisation mechanism such that it enables images to be acquired under the control of this synchronisation system which will be generated by a monitoring signal for a physiological constant, such as respiration or the heartbeat, in order to be able to eliminate the movement caused by the displacement of certain organs, in the case of the example the lungs and heart, so that the image obtained has the greatest clarity on having eliminated the movement as a source of blurring.

BRIEF DESCRIPTION OF THE FIGURES

A more detailed explanation of the invention is given in the following description based on the attached figures in which.

DESCRIPTION OF THE INVENTION

Figure 1:
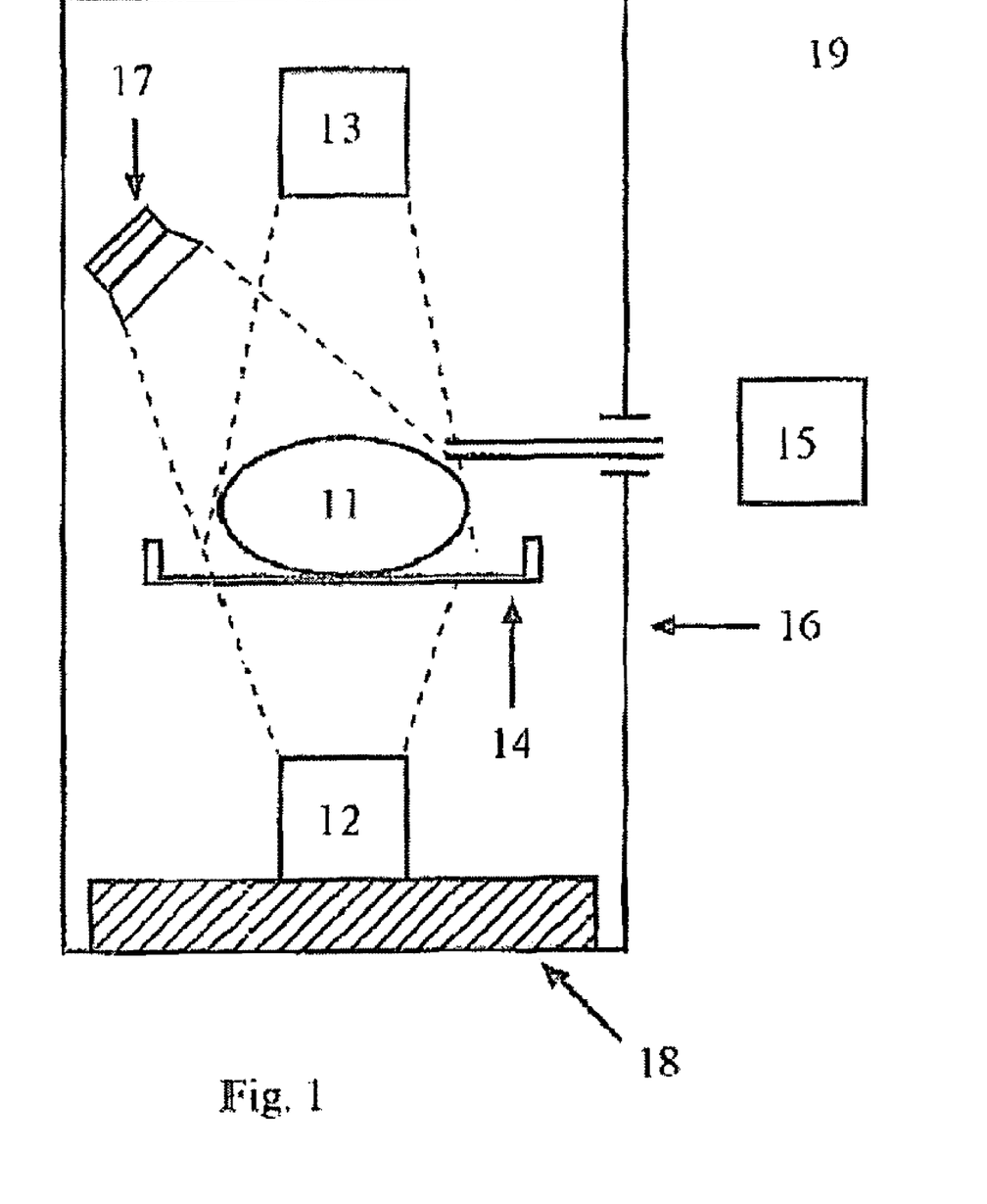
FIG. 1 shows a block diagram of an incubator as per the invention.

With reference to FIG. 1, a block diagram of an incubator 19 is illustrated, which comprises an imaging system 12, 13, 17 which enables images to be obtained of a subject 11 submitted to study located inside an incubator, without using ionising radiation, which is harmful to some young, immature subjects 11.

The incubator comprises a first detector of non-ionising radiation 12, a first emitter of non-ionising radiation 13, for example a coherent light laser, a support bed 14 for the subject 11 under study, it being possible to observe the subject through a window transparent to radiation, a set of equipment for life support 15, comprising at least control for temperature, gases, heart monitoring, respiration monitoring, extraction of liquids, feeding, etc; a light screen 16 to prevent undesired external illumination reaching the detectors or sampling, so contaminating the measurements; a second illuminator/detector of non-ionising radiation 17 operating in reflection mode, for example diffuse light; an anti-vibration support 18 for isolation from the outside.

The imaging system provides various modes of operation, for example, the first emitter 13 emits and the first receiver 12 and the second emitter/receiver 17 receive. Another operating option is for the first emitter 13 to emit and the second emitter/receiver 17 to receive. The second emitter/receiver 17 can also both emit and receive. A new mode of operation is for the second emitter/receiver 17 to emit and the first receiver 12 to receive.

The imaging system 12, 13, 17 also enables the positioning to be obtained of an instrument which may be moved within the body of the subject 11 under study and immobilised within the incubator. Therefore, it is possible to view the position of the different types of probes which are capable of being inserted in the body of the subject under study. These probes may belong to a system for assisted breathing, for monitoring a physiological signal, for draining liquids, for feeding or similar.

The imaging system 12, 13, 17 uses non-ionising radiation, such as ultrasound, electromagnetic energy in the visible light and infrared range and in the radiofrequency range, which as a consequence of being applied to subjects such as newborn babies and subsequently detected by devices provided for the purpose 12, 17, produces an image with relevant information for their diagnosis or treatment.

The type of subject 11 submitted to study seriously limits the type of technology which can be used to position a probe within their body. Imaging techniques which use non-ionising radiation enable newborn babies to be supervised and cared for in intensive care units or rehabilitation units without their use being limited by the dose of undesirable harmful radiation.

The imaging system 12, 13, 17 incorporated in the incubator 19 generates photons of non-ionising radiation by means of the first source 13, to wit an illuminating medium in the range of light from the limit of the ultraviolet to the far infrared, which is projected onto the subject 11 under study into whom at least one probe is inserted.

The photons projected onto the subject 11 are received by the first receiver 12, to wit a detecting medium which converts the energy of each photon reflected, refracted or dispersed by the subject and the probe, into an electrical signal which is sent to a medium for processing the output signal generated by the receiving medium 12, 17, which generates a projected or tomographic, anatomical or functional image to be displayed on a first screen, such as a computer screen.

The first illuminator 13 and the first detector 12 are located at opposite sides of the subject 11 under study, for example, when working in transmission mode. They may also both be on the same side of the subject in similar positions, such as shown for example in FIG. 1, in which the illuminator 13 is alongside the second detector 17, while the first receiver 12 is on the other side, symmetrically or not, of the subject 11 under study.

The subject 11 under study is supported on the tray 14 included in the incubator 19, which, in the case of working in transmission mode, will have the appropriate optical properties of maximum transmission and minimum reflection as a function of the physical properties of the first illuminator 13 used.

Obviously, the subject 11 is connected to the life support system 15 included in the incubator 19. Normally, incubators have this support equipment for the maintenance of the subject's vital signs.

Given the physical characteristics of the first illuminator 13 and the first detector 12, the incubator 19 includes a cover medium 16 to block a possible external light source which would interfere with the light beam emitted by the first illuminator 13, detracting from the detection process.

A system of supervision incorporated by the incubator enables the subject's condition to be supervised in real time using images such as video, infrared, stereoscopic or similar images. These may be varied depending on the specific need of the implementation. This system may be a part of the detector itself or may be another independent device.

An anatomical image needs to be understood as one whose composition depends on the physical structure or morphology of the subject under study, while a functional image is understood as an image whose composition obeys a given static or dynamic biological process, the organisation and spatial distribution of which does not need to correspond to a given anatomical or organic form, and whose source of contrast may respond to an endogenous phenomenon or a phenomenon produced by the presence of some type of tracer which was previously injected into the subject under study.

The use of the imaging system based on photons of non-ionising radiation enables simplification of the construction of the incubator 19 incorporating the aforementioned imaging system 12, 13, 17, as the requirements which it has to fulfil as regards shielding to restrict scattered radiation are less demanding than those which would derive from the use of X-ray equipment incorporated in the incubator.

The display of the inside of the body of newborn babies is limited by the dose of X-rays, ionising radiation, to which the subject can be exposed, as well as by the handling to which they can be submitted.

The use of non-ionising imaging equipment enables the frequency of its use as applied to the subject under study to be increased. Furthermore, it enables different applications to be used, such as anatomical imaging, functional imaging and the application of different examination conditions.

Figure 2:
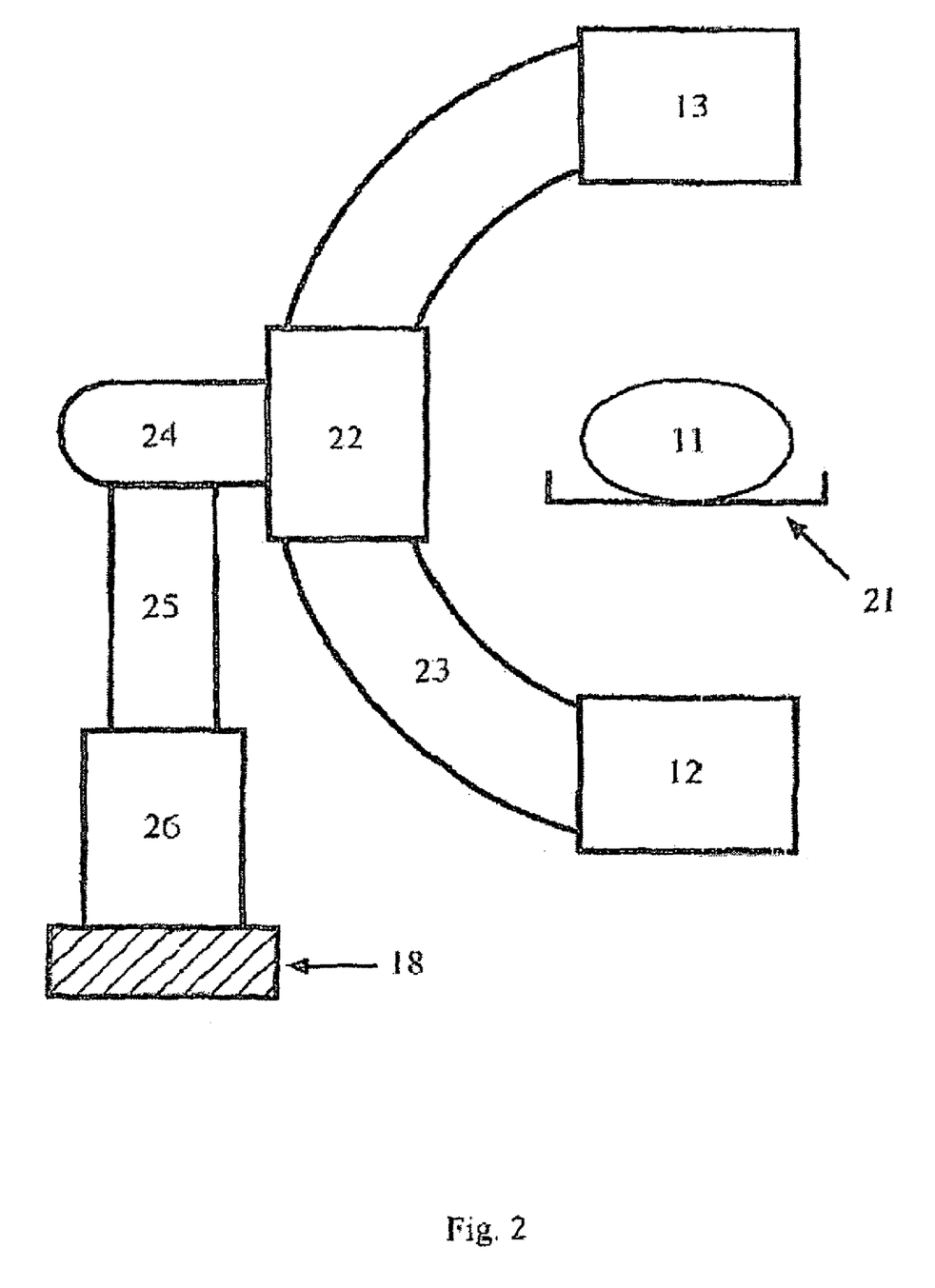
FIG. 2 shows a system of articulated arms in a C shape which comprises elements which detect and emit non-ionising radiation as per the invention.

In relation to FIG. 2, the subject 11 supported by the bed 14 adapted to his or her size and geometry and with a window transparent to the radiation used 21, is suspended between the ends of a C-shaped arm 23, in which the first source 13 of non-ionising radiation and the first detector 12 are housed.

In turn, the C-shaped arc 23 can rotate on a first articulation 22 of a ball type, while the arc 23 part can move telescopically on its symmetrical part, enabling the arc 23 to be opened or closed.

This whole assembly is supported in turn by a second motorised ball-type articulation 24 which enables rotation on the base made up of the assembly 25, 26, 18. This support assembly 25, 26, 18 comprises the solid anti-vibration base 18 on which a support 26 houses a telescopic assembly 25 which enables the regulation of the height above the ground of the arc assembly 23, the first illuminator 13 and the first detector 12, providing several degrees of freedom, understood as degrees of movement to locate the first illuminator 13 and detector 12 in a wide range of positions relative to each other and with respect to the subject 11.

Figure 3:
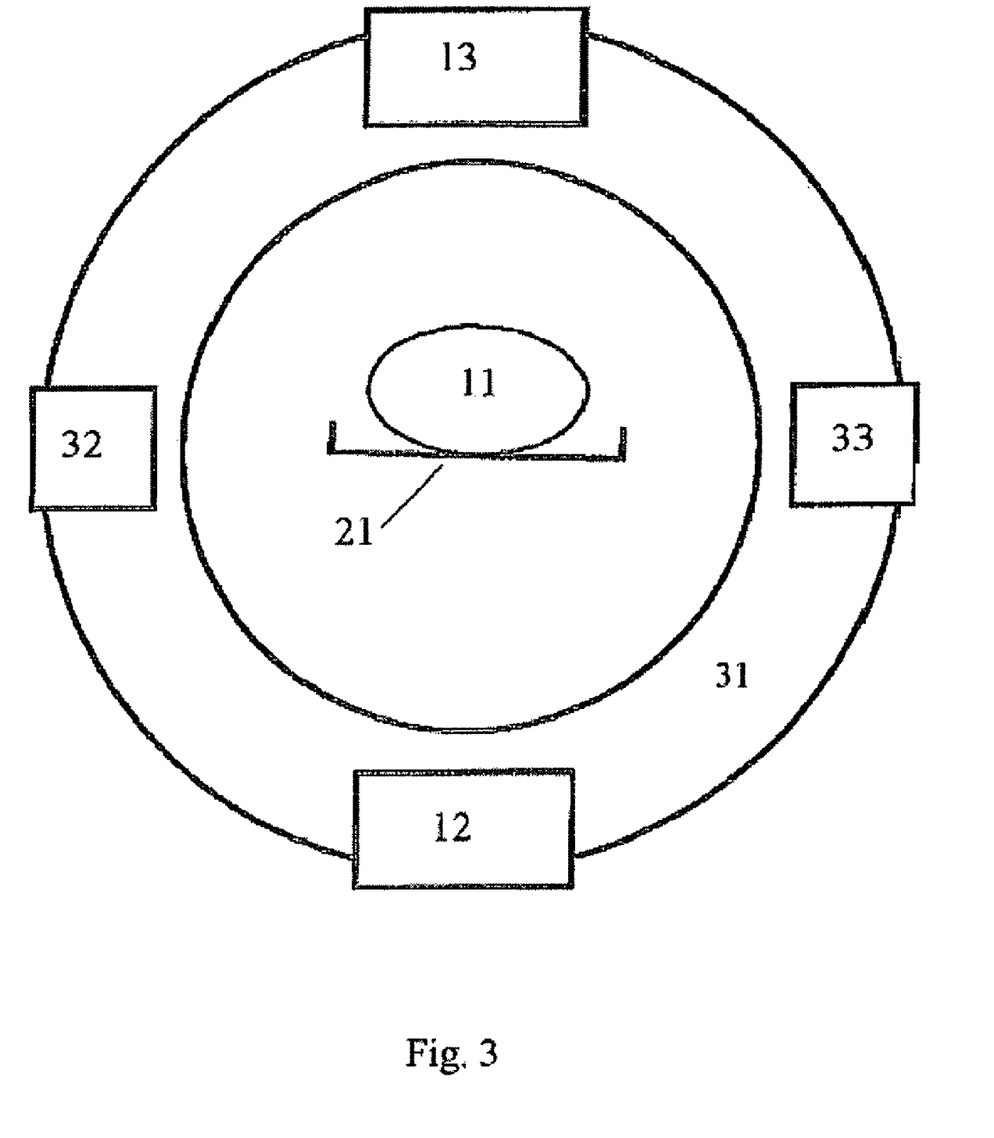
FIG. 3 illustrates an alternative system for supporting the illumination and capture elements, in the form of a rotating disc, leaving space to house elements belonging to another imaging mode as per the invention.

FIG. 3 shows a rotating ring 31 in which the first emitter 13 and the first detector 12 of non-ionising radiation are located in positions diametrically opposed such that the subject 11 and the transparent support 21 which holds him or her are at the centre of rotation of the system 31, while on the axis orthogonal to that defined by the first emitter 13 and the first detector 12 there is another assembly made up of third and fourth 32, 33 detectors of other types of radiation or an emitter/receiver assembly for another type of radiation different to that used in the primary system, with it being possible for this second type of radiation to be of any type such as ionising radiation or not, or mechanical radiation.

Figure 4:
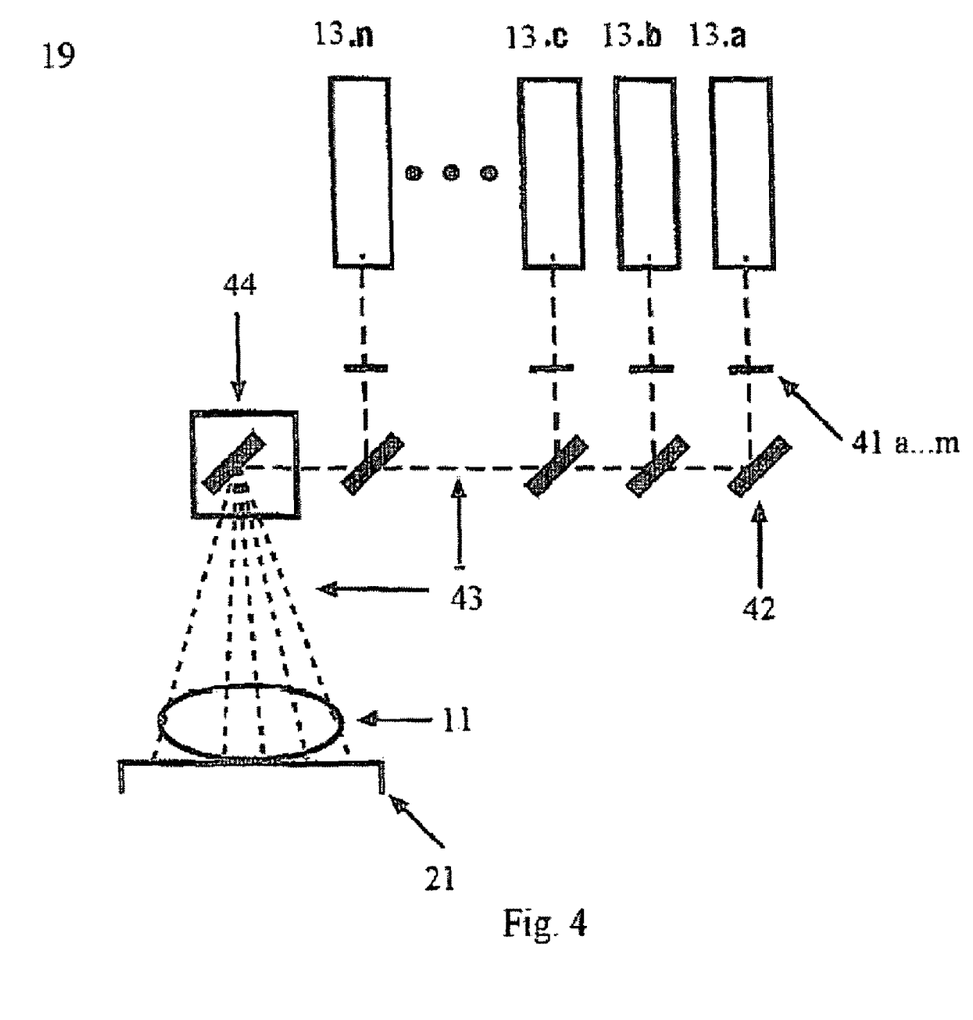
FIG. 4 shows a form of making a first source of illumination with means to control the wavelength of the non-ionising radiation as well as the position at which it points as per the invention.

FIG. 4 shows an embodiment of the first source of illumination 13 with means to control the wavelength of the non-ionising radiation, as well as the position at which it points.

The first source 13 comprises an assembly of lasers of differing wavelengths, that is, a bank of different lasers 13a, 13b, ..., 13n with their respective shutters 41x which are focused on a beam orientation device 44 by means of an assembly of mirrors 42, such that the subject under examination 11 can be examined by the beam 43 by means of the deflection of the device. In the transmission operating mode, the patient support 21 includes the corresponding window.

Figure 5:
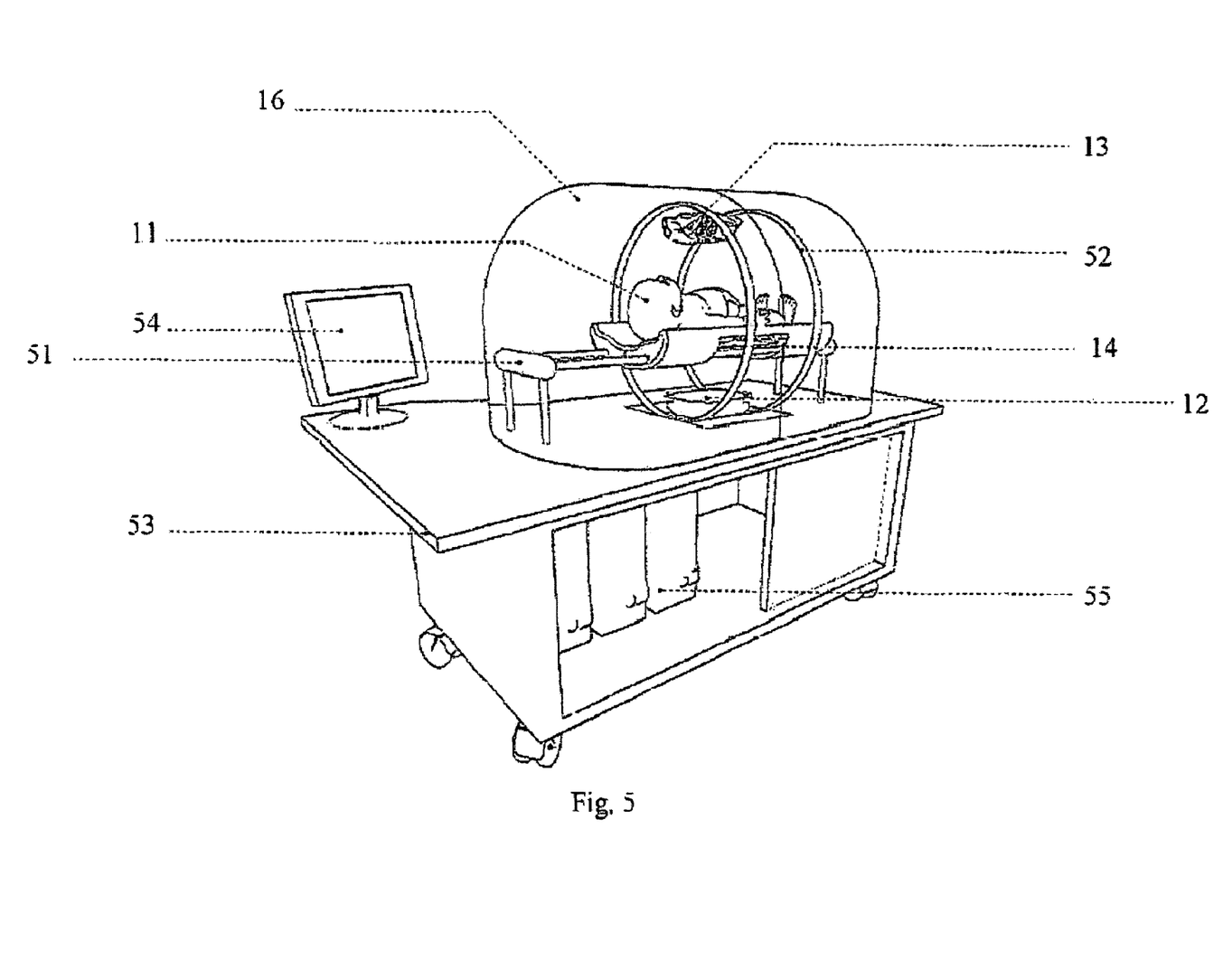
FIG. 5 shows a perspective view of what would be the complete system integrated into a practical embodiment, illustrating the location of the patient, the emitting and detecting systems, the life support systems for the subject under study and all the electronic and electromagnetic equipment necessary for the operation of the incubator as per the invention.

A perspective view is shown in FIG. 5, where the subject 11 is supported by the bed 14 which has the window 16 which is transparent to the radiation and which can be moved by means of the guides 51. An assembly of rotating rings 52 supports the first light emitter 13 and the first receiver 12.

The system is supported on a surface 18 which isolates it from the vibrations from the outside, under which the electronic and electromechanical modules 55 for the imaging system are housed, along with those for life support and monitoring of the subject.

On top of the surface 18 there is the screen 16 which isolates the subject from external light during the time of the examination. This screen can be removed or retracted by means of the corresponding mechanism so as to permit access to the subject 11 by health care personnel.

The system is controlled using a touch screen 54, on which the results are also displayed for viewing. This touch screen can be replaced by a combination of a normal screen plus mouse and keyboard or other type of user interface.

Figure 6:
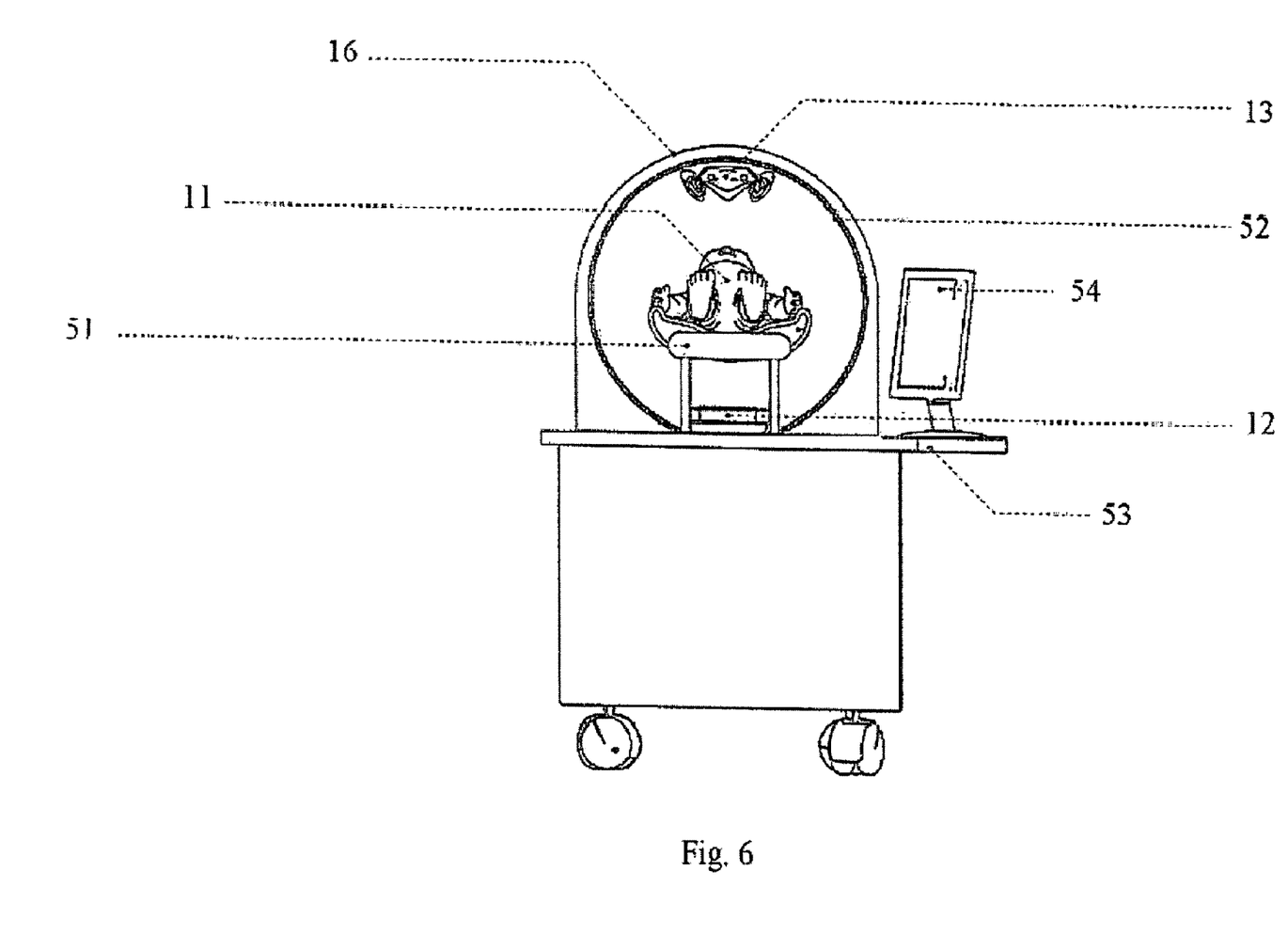
FIG. 6 shows a view in elevation of the incubator as per the invention.
Figure 7:
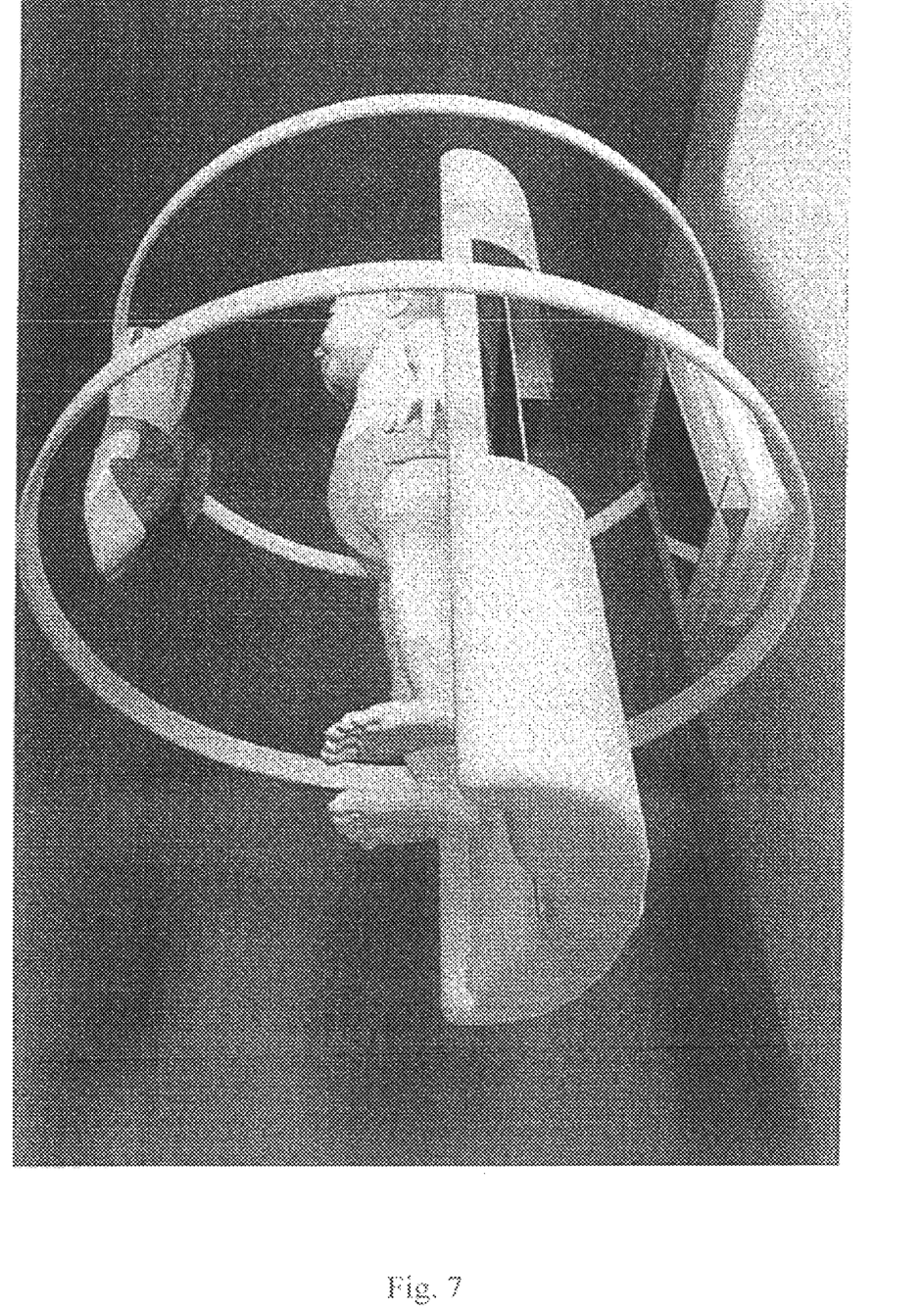
FIG. 7 shows a three-dimensional view of the incubator as per the invention.

FIG. 6 shows a side view of the assembly represented in FIG. 5. FIG. 7 shows a three-dimensional view of the subject 11 on the bed 14 in the internal space of the incubator 19.

A medical imaging system for newborn babies and breast-feeding babies using photons, electromagnetic radiation, of non-ionising radiation, coherent or non-coherent, collimated or not, and its properties of transmission and dispersion in biological tissue, turbid media, fluorescence, luminescence or bioluminescence, applies methods for the formation and reconstruction of images, which may include but are not limited to projective or tomographic imaging techniques, system modelling using any type of equations such as statistics, Maxwell's equations, Green's functions, etc, inversion of the reconstruction problem to obtain both projection and tomographic three-dimensional images, either static or dynamic, or contrast images, whatever the mechanism used to achieve this contrast, whether endogenous, exogenous, using mathematical procedures for manipulating the data acquired under different conditions, at different times, etc.

The embodiment and example stated in this record is presented as the best explanation of this invention and its practical application and to enable an expert in the field to put the invention into practice and use it. However, the expert in the field will recognise that the description and example above have been presented with the purpose of illustration and only as an example.

The invention claimed is:

1. An incubator for imaging with non-ionising radiation for the care of newborn babies; characterized in that the incubator comprises at least a first detector of non-ionising radiation (12); at least a first emitter of non-ionising radiation (13); a bed (14) for supporting a subject (11) under study, it being possible to observe the subject through a window transparent to radiation; life support equipment (15) comprising at least a control for temperature, gases, heart monitoring, respiratory monitoring, extraction of liquids, and feeding; a medium for screening (16) light to prevent interference from illumination from outside of the incubator (19); at least a second illuminator/detector of non-ionising radiation (17) operating in reflection mode which optionally incorporates its own light source; an anti-vibration support (18) for isolating the incubator and the subject from the outside; and an imaging system comprising projective, and/or tomographic imaging, and which imaging system utilizes non-ionising radiation in the band of the electromagnetic spectrum comprising between ultraviolet light and the far infrared, enabling the viewing of the subject (11) located on the bed (14) such that the projective and/or tomographic image is morphological and/or functional.

2. An incubator according to claim 1; characterized in that the first detector of non-ionising radiation (12), the first emitter of non-ionising radiation (13), the screening medium (16), and the second illuminator/detector of non-ionising radiation (17) are adapted to be movable with respect to the subject (11) under study and/or with respect to each other.

3. An incubator according to claim 2; characterized in that the incubator (19) is constructed and adapted to prevent alterations in the vital signs of the subject (11) under study.

4. An incubator according to claim 3; characterized in that the incubator (19) comprises means of rotation constructed and adapted so that the imaging system can register a set of data in the form of projections which are processed by means of a tomographic reconstruction method adapted to the properties of the radiation used.

5. An incubator according to claim 4; characterized in that the contrast in the image obtained is determined by the distribution of a tracer previously injected into the subject (11) under examination.

6. An incubator according to claim 5; characterized in that the incubator (19) comprises a multispectral source of radiation selected from the group consisting of coherent radiation, non-coherent radiation, collimated radiation and non-collimated radiation such that the response of the tissue under study is different at different wavelengths, enabling images to be generated according to the different properties depending on the frequency.

7. An incubator according to claim 6; characterized in that the incubator (19) uses a combination of imaging techniques by means of non-ionising electromagnetic radiation with another medical imaging technique selected from the group consisting of electromagnetic energy radiation and mechanical energy.

8. An incubator for a newborn, comprising:
an imaging assembly for obtaining images of a newborn under study and located in the incubator, the imaging assembly comprising a non-ionizing radiation imaging system;
a support for supporting the newborn in the incubator;
a life support system associated with the newborn for detecting and monitoring the vital signs of the newborn;
a light screening medium associated with the support and the newborn for screening light to prevent interference to the non-ionizing radiation imaging system from external illumination; and
an anti-vibration support associated with the imaging assembly for isolation from the external environment.

9. The incubator of claim 8 wherein the non-ionizing radiation imaging system further comprises:
a first emitting device for emitting non-ionized radiation ;
a first detecting device for receiving the non-ionizing radiation of the first emitting device; and
a second device for emitting or detecting non-ionizing radiation and operating in a reflection mode relative to the first emitting device and the first detecting device and optionally including a light source.

10. The incubator of claim 9 wherein the non-ionizing radiation imaging system further comprises non-ionized radiation in the band of the electromagnetic spectrum comprising that between ultraviolet light and the far infrared; wherein the non-ionizing radiation imaging system comprises a projective imaging system and/or a tomographic imaging system; and wherein the projective image or the tomographic image of the non-ionizing radiation imaging system comprises a morphological image and/or a functional image.

11. The incubator of claim 9 wherein the non-ionizing radiation imaging system is constructed and arranged to be movable relative to the newborn.

12. The incubator of claim 9 wherein the first non-ionized radiation emitting device and the first non-ionized radiation detecting device are carried by a movable C-shaped arm; and wherein the first non-ionized radiation emitting device and the first non-ionized radiation detecting device are optionally positioned diametrically opposite to the newborn.

13. The incubator of claim 9 wherein the first non-ionized radiation emitting device and the first non-ionized radiation detecting device are carried by a rotatable ring; and wherein the first non-ionized radiation emitting device and the first non-ionized radiation detecting device are locatable in positions diametrically opposite to each other and to the newborn.

14. The incubator of claim 9 wherein the imaging assembly further comprises a second radiation imaging system comprising devices for emitting and/or detecting energy selected from the group consisting of electromagnetic energy and mechanical energy.

15. The incubator of claim 9 wherein the first non-ionizing radiation emitting device comprises a laser assembly.

16. The incubator of claim 9 wherein the first non-ionized radiation emitting device, the first non-ionized radiation detecting device, the medium for screening light, and the second non-ionized emitting device/detecting device are constructed and adapted to be movable relative to the newborn and/or relative to each other.

17. The incubator of claim 9 wherein the incubator is constructed and adapted to prevent alterations in the vital signs of the newborn.

18. The incubator of claim 8 wherein the incubator further comprises rotatable means constructed and adapted so that the imaging assembly can register a set of data in the form of projections which are processed by means of a tomographic reconstruction method adapted to the properties of the type of radiation used in the first radiation imaging system and the second radiation imaging system.

19. The incubator of claim 8 wherein a contrast in the image obtained by the imaging assembly is determined by the distribution of a probe injected into the newborn under study.

20. The incubator of claim 8 wherein the incubator further comprises a multispectral source of radiation selected from the group consisting of coherent, non-coherent, collimated and non-collimated radiation such that the response of the tissue of the newborn under study is different at different wavelengths thereby enabling images to be generated according to the different properties depending on the frequency of the radiation of the imaging assembly.

21. The incubator of claim 9 wherein the incubator further comprises an assembly of rings arranged around the newborn and the support supporting the newborn constructed and adapted to support the first emitting device and the first detecting device of the non-ionizing radiation imaging system.

* * * * *